(12) United States Patent
Meyer

(10) Patent No.: US 7,443,954 B2
(45) Date of Patent: Oct. 28, 2008

(54) X-RAY MACHINE

(75) Inventor: Andreas Meyer, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 225 days.

(21) Appl. No.: 10/892,347

(22) Filed: Jul. 16, 2004

(65) Prior Publication Data
US 2005/0013408 A1   Jan. 20, 2005

(30) Foreign Application Priority Data
Jul. 17, 2003   (DE)   ................ 103 32 596

(51) Int. Cl.
*H05G 1/64* (2006.01)
(52) U.S. Cl. .................. 378/98.3; 378/98.7; 378/98.9
(58) Field of Classification Search ........... 378/98.2, 378/98.3, 98.5, 98, 98.7, 98.8, 114, 115, 378/116, 37, 38, 39, 40, 62; 250/214, 201.1, 250/201.2, 370.09; 382/130, 148, 128, 132
See application file for complete search history.

(56) References Cited

U.S. PATENT DOCUMENTS

| | | | |
|---|---|---|---|
| 4,146,794 A * | 3/1979 | Duinker ..................... 378/7 |
| 4,360,731 A * | 11/1982 | Fink et al. .................. 378/108 |
| 5,022,063 A * | 6/1991 | Yokouchi et al. ........... 378/98.2 |
| 5,155,753 A * | 10/1992 | Kuetterer .................... 378/98.3 |
| 5,394,455 A * | 2/1995 | Roeck et al. ............... 378/98.3 |
| 5,473,659 A * | 12/1995 | Haendle et al. ............. 378/98.2 |
| 5,485,500 A * | 1/1996 | Baba et al. .................. 378/98.2 |
| 5,506,880 A * | 4/1996 | Scardino et al. ............ 378/98.2 |
| 5,592,524 A * | 1/1997 | Roper et al. ................ 378/98.2 |
| 5,594,771 A * | 1/1997 | Kawai ........................ 378/98.2 |
| 6,285,738 B1 * | 9/2001 | Nagai et al. ................ 378/98.8 |
| 6,301,331 B1 * | 10/2001 | Yokouchi et al. ........... 378/98.3 |
| 2001/0036248 A1 * | 11/2001 | Yokouchi et al. ........... 378/98.3 |
| 2002/0196899 A1 * | 12/2002 | Karellas ..................... 378/98.8 |

FOREIGN PATENT DOCUMENTS

DE    35 26 687 A1    3/1986
GB    2 186 149 A     8/1987

OTHER PUBLICATIONS

R. F. Schulz, "Fortschritte auf dem Gebiet der Röntgenstrahlen und der bildgebenden Verfahren" ["Advances in the field of X-rays and imaging methods"], vol. 173, 2001, Offprint, Georg Thieme Verlag Stuttgart, pp. 1137 to 1146.

* cited by examiner

*Primary Examiner*—Irakli Kiknadze
(74) *Attorney, Agent, or Firm*—Harness, Dickey & Pierce, P.L.C.

(57) ABSTRACT

An X-ray machine includes a radiation source and an image intensifier. A digital camera is downstream of the image intensifier and includes a pixel matrix, wherein the pixel matrix is switchable between a high and a low resolution. The image intensifier displays on an output screen, an image that is dependent on the incident X-radiation and that is picked up by the camera. Imaging behavior of the image intensifier, and thus the sharpness of the image displayed on the output screen, vary depending on the resolution set for the camera.

15 Claims, 1 Drawing Sheet

X-RAY MACHINE

The present application hereby claims priority under 35 U.S.C. §119 on German patent application number DE 103 32 596.4 filed Jul. 17, 2003, the entire contents of which are hereby incorporated herein by reference.

FIELD OF THE INVENTION

The invention generally relates to an X-ray machine. It may further relate to an X-ray machine having a radiation source and an image intensifier TV chain with a digital camera which is downstream of the image intensifier and a pixel matrix. Preferably, it is possible to switch the pixel matrix between a high and a low resolution. Further, the image intensifier may display on an output screen, an image that is dependent on the incident X-radiation and is picked up by the camera.

BACKGROUND OF THE INVENTION

X-ray machines having a resolution that can be switched over on the camera side are preferably applied for photographing the heart or regions near the heart. As a rule, it is possible on the camera side to switch over between a pixel matrix with high resolution of, for example, 1024×1024 pixels, and a matrix with low resolution of, for example, 512× 512 pixels, the reduction in resolution being performed by pixel binning. The advantage of this switchover resides, firstly, in that at a high image rate it is possible to reduce the detected data volume as a consequence of the reduction in resolution by comparison with the high-resolution matrix, a loss in resolution necessarily being accepted in the process. A further advantage is the lower noise by comparison with the high resolution, that is to say the noise component or the quantum noise is less for the low-resolution matrix.

However, even when a low resolution is set, the noise component still constitutes a problem that, in particular, raises difficulties for the physician observing the recorded image, since the image is noisy and unsteady.

DE 35 26 687 A1 relates to an X-ray diagnosis unit having an image intensifier with the aid of which an X-ray image generated by radiation with X-rays through an object to be examined is converted into a visible image. Also provided is a television camera that has a camera tube and serves for converting the photograph into a TV video signal.

So that an optimal image of a part of an object to be examined can be obtained, a control unit is provided via which the diameter of the photograph of the image intensifier, and the scanning area of the camera tube can be controlled in an interlocking fashion. The output signal or dynamic range and response time behave reciprocally relative to one another in a camera tube, and so it is the aim of D1 to render it possible with a single camera tube to obtain an image selectively with high resolution or a good response time.

The diameter of the photograph of the image intensifier is varied for this purpose. In accordance with the diameter of the photograph, the scanning area on the photocathode can be varied, and so it can, for example, be decreased given a reduced diameter such that the signal output current of the camera tube becomes smaller. The response time can be improved thereby. A reverse procedure is appropriate when a high resolution is desired.

Digital X-ray detector systems, in particular solid state detector systems, are described in "Fortschritte auf dem Gebiet der Röntgenstrahlen und der bildgebenden Verfahren" ["Advances in the field of X-rays and imaging methods"], volume 173, 2001, Offprint, Georg Thieme Verlag Stuttgart, pages 1137 to 1146, the contents of which are hereby incorporated herein by reference. However, with solid state detectors the sharpness of the image on the output screen is entirely unable to be varied by being switched over depending on the resolution set for the camera.

GB 2 186 149 A concerns the image differentiation by using charge-coupled components with masked pixels that are opaque to the radiation to which they are exposed. They further later serve as storage areas for the charge pattern of the unmasked pixels which are likewise provided.

SUMMARY OF THE INVENTION

An embodiment of the invention involves specifying an X-ray machine of the type mentioned at the beginning, with which the noise component is improved even when a low resolution is set.

In the case of an X-ray machine having the features mentioned at the beginning, the imaging behavior of the image intensifier, and thus the sharpness of the image displayed on the output screen, may be different depending on the resolution set for the camera. As such, the noise component may be improved even when a low resolution is set.

In the case of the X-ray machine according to an embodiment of the invention, it is not only the resolution of the camera that may be variable, but also the imaging behavior of the image intensifier. Further, associated therewith, the sharpness of the image displayed on the output screen and recorded by the camera may be variable. The imaging behavior is a function of the camera resolution set. Thus, the output screen of the window may be provided with an imaging sharpness that can be switched over and may be adapted to the selected camera resolution.

The advantageous result of the loss in sharpness deliberately caused thereby during switching over from the high-resolution to the low-resolution matrix as a consequence of the switchover in sharpness at the image intensifier includes the fact that it is possible, with the same dose per image, to reduce the noise in the matrix of lower resolution. Further, the physician is thereby supplied overall with a less unsteady image for his surgical examination techniques. The noise is therefore reduced, and the noise impression is matched to the image matrix respectively set.

The imaging behavior is switched over in the case of an X-ray image intensifier by appropriate control of the electronic optics via which the electrons generated at the input screen by the incident X-radiation are accelerated onto the output screen and thereby imaged.

A further problem relating to a camera resolution which can be switched over and which arises from known X-ray machines of the type under discussion resides in the fact that, owing to the low dose rate or dose per image, switching over to the low-resolution matrix gives rise to disturbing, so-called aliasing effects. Further, or alternatively, the existing aliasing effects may be intensified and become clearly visible.

Aliasing effects occur for the most part, but are more strongly pronounced given a lower dose than for photographs, with a higher dose. Aliasing effects are image artifacts that are caused by aliasing of higher-frequency signal components including a noise component from a spatial frequency band that is above the so-called Nyquist rate or Nyquist frequency. If a sampling system, such as an image intensifier camera system for example, fulfills the so-called Nyquist condition, it is possible by way of downstream signaling processing to recover the original input signal without error. That is to say the image signal originally incoming at the input screen is to this extent reproduced without error and without artifacts caused by aliasing. The Nyquist condition and the physical relationships are known per se and require no explanation in greater detail.

If a switchover is now made to the low-resolution pixel matrix from the high-resolution pixel matrix with respect to which the imaging behavior of the image intensifier is optimized per se in the case of the known X-ray machines with switchable camera resolution, the substantial aliasing effects described result because the Nyquist condition of the X-ray image intensifier is not adapted with reference to the resolving power of the camera. Therefore, the Nyquist condition is thus also no longer fulfilled.

An improvement results from the change, provided by an embodiment of the invention, in the imaging behavior of the X-ray image intensifier and from the unsharpness setting specifically associated therewith. Further, this specific change in the imaging sharpness also influences the modulation transfer function (MTF) of the image intensifier, specifically lowers it. It is already thereby possible to reduce substantially the signal component that is undesirably introduced anyway by aliasing.

A further-reaching improvement is achieved according to an embodiment of the invention, by virtue of the fact that at a resolution of low setting the imaging behavior of the image intensifier is such that the modulation transfer function of the image intensifier, which is influenced by the change in the imaging behavior and thus in the imaging sharpness, permits a largely artifact-free imaging up to above the Nyquist limit of the selected resolution, whereas signal components of higher frequency are imaged only up to a frequency that corresponds substantially to the lowest frequency of aliased signal components. That is to say, the useful signal area that can be imaged is limited to a frequency range that reaches as far as the frequency range within which there are located aliased signal components that therefore cannot be transmitted. Thus, the unsharpness is selected in such a way, and therefore also the modulation transfer function is set and optimized in such a way, that objects up to the Nyquist limit or Nyquist frequency of the low-resolution matrix, such as the 512 matrix for example, are still transmitted. Further, higher-frequency components including aliased components are no longer transmitted.

Overall, the switchover according to an embodiment of the invention and the selection, proposed according to an embodiment of the invention, of the switchover point or of the imaging behavior result in a representation of the image with the aid of the low-resolution matrix that clearly has less noise and is largely free of artifacts.

It is particularly expedient when the setting of the required imaging behavior of the image intensifier is performed automatically when selecting the desired camera resolution. Thus, the imaging behavior of the image intensifier is automatically adapted and set to the selected camera resolution. Accordingly, two defined imaging functions that are set automatically are given for the two defined resolutions.

It may be pointed out at this juncture that it is also possible, of course, for the pixel matrix to be switched not only between two resolutions, but also, if appropriate, between a plurality of resolutions. In this case, it is expedient for the X-ray image intensifier to define imaging functions, or defined imaging parameters, that correspond to all the resolution settings and are set automatically.

BRIEF DESCRIPTION OF THE DRAWINGS

The present invention will become more fully understood from the detailed description of preferred exemplary embodiments given hereinbelow and the accompanying drawing, which is given by way of illustration only and thus are not limitative of the present invention, and wherein.

DETAILED DESCRIPTION OF THE PREFERRED EMBODIMENTS

Figure 1:
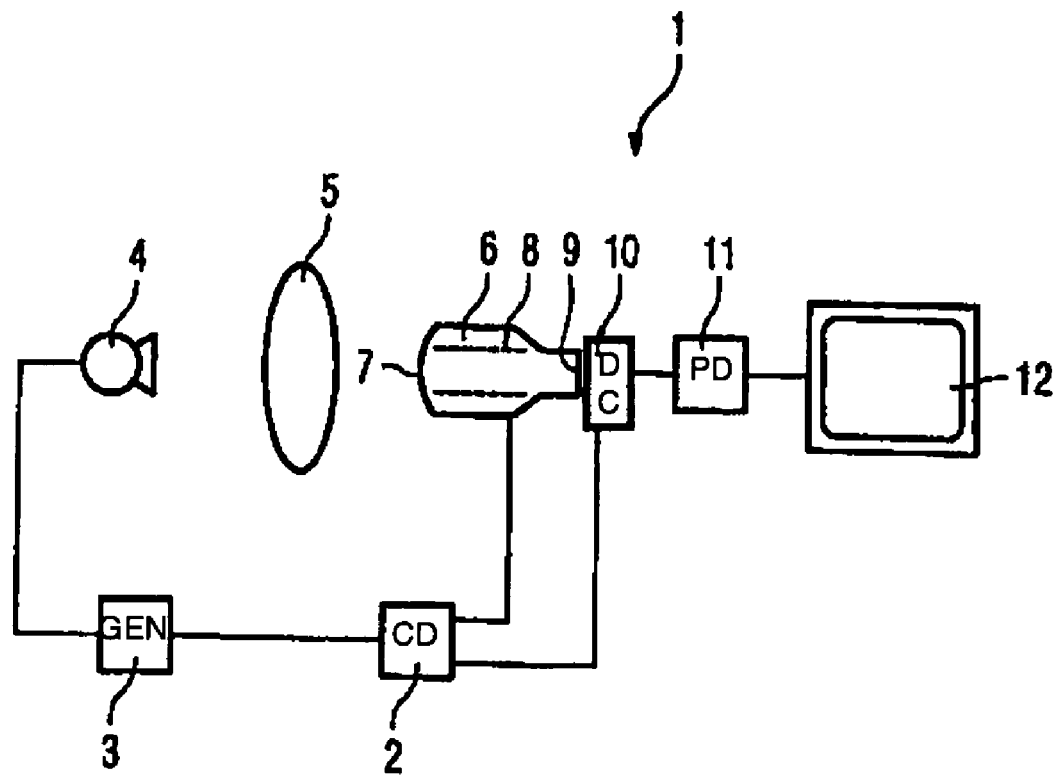
FIG. 1 shows a block diagram of an X-ray machine according to an embodiment of the invention.

FIG. 1 shows an X-ray machine 1 according to an embodiment of the invention, including a central control device 2 that controls the operation of the relevant components and via which a generator 3 that operates an X-ray source 4 is controlled. The source emits X-radiation that penetrates an object 5. The transmitted X-radiation strikes an X-ray image intensifier 6, where it is converted at the input screen 7 into electrons that are focused via electron optics 8 integrated in the X-ray image intensifier and accelerated onto an output screen 9 where they are converted, in turn, into visible light.

Thus, an image that depends on the incident X-radiation is displayed on the output screen 9. This image is recorded by a digital camera 10, specifically a CCD camera, with the aid of a pixel matrix. The camera image recorded is processed via an image processing device 11, and can be output on a monitor 12.

The pixel matrix of the CCD camera can preferably be switched between two resolutions, for example from a 1024× 1024 pixel matrix to a 512×512 matrix having a lower resolution. This may be performed by suitable pixel binning, for example. This is controlled via the control device 2.

In addition to the camera resolution, the control device 2 also controls the imaging behavior of the X-ray image intensifier 6. Thus, the operation of the electron optics 8 via which the image displayed on the output screen 9 can be influenced.

In the case of the X-ray machine 1 according to an embodiment of the invention, each setting of the resolution for the camera 10 is assigned a defined imaging behavior of the X-ray image intensifier 6, or a specific set of operating parameters of the electron optics 8. Accordingly, the imaging behavior depends variously on the camera resolution set. Fundamentally, the imaging behavior is adapted to the high camera resolution, thus to 1024×1024 pixel matrix, for example. Thus, operation is carried out with optimum setting of the sharpness with reference to the high resolution. The X-ray image intensifier thus images with optimal sharpness.

If the operator now initiates a switchover to the matrix with low resolution, the control device 2 automatically selects the corresponding set of operating parameters for the changed imaging behavior of the image intensifier, and the imaging behavior is automatically switched over. This is done so specifically in such a way that an intentional unsharpness of the image displayed on the output screen 9 is set. This is attended by a number of advantages.

Firstly, the noise inside the low-resolution matrix may be thereby reduced in conjunction with the same dose per recorded image, and the physician may be displayed a steadier image with substantially less noise on the monitor 12. Secondly, it is possible by a suitable selection of the imaging behavior and thus of the modulation transfer frequency influenced thereby to prevent mirror products, so-called artifacts, that are situated above the Nyquist limit of the high-resolution matrix from being reflected into the useful signal area and additionally raising the noise in the image recorded with the aid of the low-resolution matrix.

Figure 2:
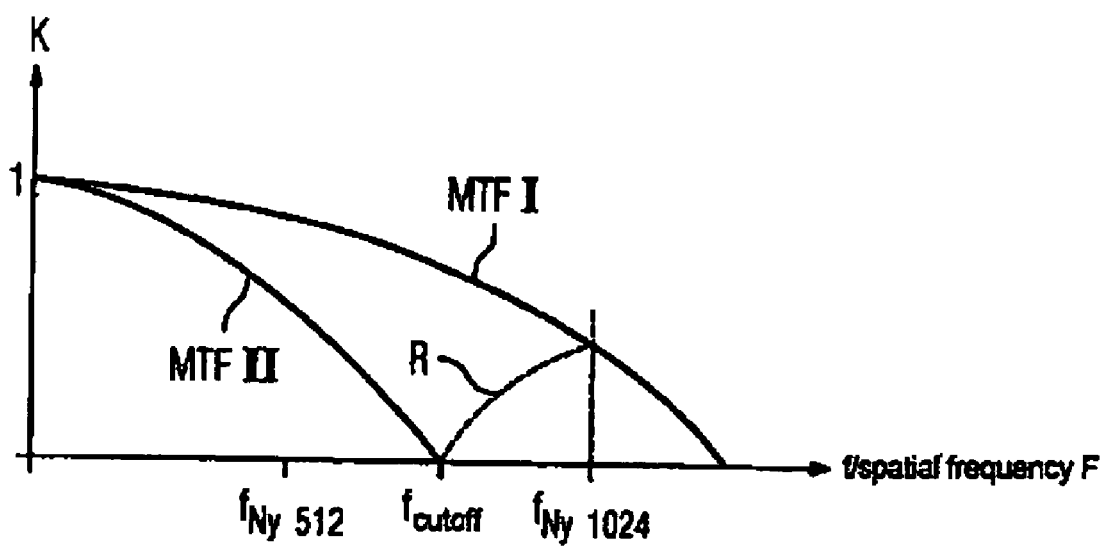
FIG. 2 shows a diagram to illustrate the changing modulation transfer function of the image intensifier through a change in the sharpness setting.

This function follows from FIG. 2. What is shown is a diagram in which the transfer ratio K is plotted along the ordinate, and the spatial frequency F and the Nyquist frequency $f_{Ny}$ of the different matrices set are plotted along the abscissa.

Two modulation transfer functions MTF I and MTF II are shown. The modulation transfer function MTF I reproduces the function for an optimum setting of sharpness for the X-ray image amplifier 6, referring to the customary operating mode with camera resolution set high. The modulation transfer function extends into a spatial frequency region that is substantially above the Nyquist limit or Nyquist frequency $f_{Ny1024}$ for the high-resolution camera setting (starting from a pixel matrix 1024×1024).

If the camera resolution is now switched over to a 512×512 matrix, and if the imaging behavior and thus the modulation transfer function of the X-ray image intensifier 6 are not changed (the curve in accordance with MTF I thus being adhered to), then—since the Nyquist limit or Nyquist frequency $f_{Ny512}$ of the low-resolution 512×512 matrix is substantially below the corresponding Nyquist frequency of the high-resolution 1024×1024 matrix—undesired instances of aliasing occur for those spatial frequency components that are above the Nyquist frequency of the 1024×1024 matrix. This is illustrated by the dashed line R, which shows the aliased signal component. This aliased signal component leads to undesired image artifacts and causes the so-called aliasing effect.

As already described, the imaging behavior of the X-ray image intensifier 6 is now changed in the X-ray machine 1 according to an embodiment of the invention. Specifically, it may be changed in such a way that the modulation transfer function MTF is reduced and selected such that signal components up to the Nyquist frequency of the low-resolution 512×512 matrix and above that are transmitted, while higher-frequency image components, and thus also aliased components, are no longer transmitted, however. This modulation transfer function is illustrated in FIG. 2 by the curve MTF II. Located where the MTF II intersects the abscissa is the cutoff frequency $f_{cutoff}$ up to which signals are transmitted; components of higher frequency are not transmitted.

Thus, firstly, specific setting of sharpness or a specific less sharp imaging on the output screen reduces the noise component. Secondly, the optimized adaptation of the modulation transfer function to the resolving power of the 512×512 matrix also avoids the occurrence of aliasing effects, that is to say the reflection of higher-frequency signal components into the useful signal area. This may be seen with the aid of the line R, which does not run into the area underneath the MTF II.

This switchover is performed automatically on the part of the control device 2 whenever the resolving power of the camera 10 is changed. Thus, it follows that operation also proceeds with the imaging behavior optimized for the respective resolving power of the camera, or with the optimized modulation transfer function.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray machine, comprising:
   a radiation source; and
   an image intensifier, wherein a digital camera is located downstream of the image intensifier and includes a pixel matrix switchable between a high and a low resolution, wherein the image intensifier is adapted to display on an output screen an image that is dependent on incident X-radiation and is picked up by the digital camera, wherein sharpness of the image displayed on the output screen varies depending on a resolution set for the digital camera.

2. The X-ray machine as claimed in claim 1, wherein at a resolution of low setting, an imaging behavior of the image intensifier is such that a modulation transfer function of the image intensifier, influenced by a change in the imaging sharpness, permits an artifact-free imaging only of signal components below a cutoff frequency that is above the Nyquist limit of a selected low resolution and corresponds to a lowest frequency of aliased signal components.

3. The X-ray machine as claimed in claim 2, wherein the setting of the required imaging behavior of the image intensifier is performed automatically when selecting the desired digital camera resolution.

4. The X-ray machine as claimed in claim 3, wherein the resolution of the digital camera is switchable between a 1024×1024 matrix and a 512×512 matrix.

5. The X-ray machine as claimed in claim 2, wherein the resolution of the digital camera is switchable between a 1024×1024 matrix and a 512×512 matrix.

6. The X-ray machine as claimed in claim 1, wherein the setting of imaging behavior, relating to image sharpness, of the image intensifier is performed automatically when selecting the desired digital camera resolution.

7. The X-ray machine as claimed in claim 6, wherein the resolution of the digital camera is switchable between a 1024×1024 matrix and a 512×512 matrix.

8. The X-ray machine as claimed in claim 1, wherein the resolution of the digital camera is switchable between a 1024×1024 matrix and a 512×512 matrix.

9. An X-ray machine, comprising:
   a radiation source, adapted to emit x-radiation;
   an image intensifier; and
   a digital camera including a pixel matrix switchable between a high and a low resolution, wherein imaging behavior of the image intensifier varies depending on a resolution set for the digital camera.

10. The X-ray machine of claim 9, further comprising:
    a controller, for determining the resolution set for the digital camera and for varying imaging behavior of the image intensifier based upon the determined resolution.

11. The X-ray machine of claim 9, wherein the image intensifier is adapted to display an image dependent upon incident X-radiation and wherein the displayed image is adapted to be captured by the digital camera.

12. The X-ray machine of claim 11, further comprising:
    a controller, for determining the resolution set for the digital camera and for varying imaging behavior of the image intensifier based upon the determined resolution.

13. The X-ray machine as claimed in claim 9, wherein at a resolution of low setting, the imaging behavior of the image intensifier is such that a modulation transfer function of the image intensifier permits an artifact-free imaging only of signal components below a cutoff frequency that is above the Nyquist limit of a selected low resolution and corresponds to a lowest frequency of aliased signal components.

14. The X-ray machine as claimed in claim 9, wherein the setting of the required imaging behavior of the image intensifier is performed automatically when selecting the desired digital camera resolution.

15. The X-ray machine as claimed in claim 9, wherein the resolution of the digital camera is switchable between a 1024×1024 matrix and a 512×512 matrix.

* * * * *